(12) United States Patent
Legrand et al.

(10) Patent No.: US 7,128,902 B2
(45) Date of Patent: *Oct. 31, 2006

(54) REDUCING COMPOSITION FOR TREATING KERATIN FIBRES, COMPRISING A PARTICULAR AMINOSILICONE

(75) Inventors: Frédéric Legrand, Courbevoie (FR); Jean-Marie Millequant, Saint-Maur des Fosses (FR)

(73) Assignee: L'Oreal, SA, Paris (FR)

( * ) Notice: Subject to any disclaimer, the term of this patent is extended or adjusted under 35 U.S.C. 154(b) by 555 days.

This patent is subject to a terminal disclaimer.

(21) Appl. No.: 10/290,208

(22) Filed: Nov. 8, 2002

(65) Prior Publication Data

US 2003/0147841 A1 Aug. 7, 2003

(30) Foreign Application Priority Data

Nov. 8, 2001 (FR) .................................. 01 14470

(51) Int. Cl.
*A61Q 5/06* (2006.01)
*A61Q 5/00* (2006.01)

(52) U.S. Cl. .................................. 424/70.122; 424/62

(58) Field of Classification Search ...................... None
See application file for complete search history.

(56) References Cited

U.S. PATENT DOCUMENTS

| | | | |
|---|---|---|---|
| 2,047,398 A | 7/1936 | Voss et al. |
| 2,261,002 A | 10/1941 | Ritter |
| 2,271,378 A | 1/1942 | Searle |
| 2,273,780 A | 2/1942 | Dittmar |
| 2,375,853 A | 5/1945 | Kirby et al. |
| 2,388,614 A | 11/1945 | Kirby et al. |
| 2,454,547 A | 11/1948 | Bock et al. |
| 2,528,378 A | 10/1950 | Mannheimer |
| 2,723,248 A | 11/1955 | Wright |
| 2,781,354 A | 2/1957 | Mannheimer |
| 2,798,053 A | 7/1957 | Brown |
| 2,923,692 A | 2/1960 | Ackerman et al. |
| 2,961,347 A | 11/1960 | Floyd |
| 3,206,462 A | 9/1965 | McCarty |
| 3,227,615 A | 1/1966 | Korden |
| 3,472,840 A | 10/1969 | Stone et al. |
| 3,589,578 A | 6/1971 | Kamphausen |
| 3,632,559 A | 1/1972 | Matter et al. |
| 3,810,977 A | 5/1974 | Levine et al. |
| 3,836,537 A | 9/1974 | Boerwinkle et al. |
| 3,874,870 A | 4/1975 | Green et al. |
| 3,910,862 A | 10/1975 | Barabas et al. |
| 3,912,808 A | 10/1975 | Sokol |
| 3,915,921 A | 10/1975 | Schlatzer, Jr. |
| 3,917,817 A | 11/1975 | Vanlerberghe et al. |
| 3,929,990 A | 12/1975 | Green et al. |
| 3,966,904 A | 6/1976 | Green et al. |
| 3,990,459 A | 11/1976 | Papantoniou |
| 4,001,432 A | 1/1977 | Green et al. |
| 4,005,193 A | 1/1977 | Green et al. |
| 4,013,787 A | 3/1977 | Vanlerberghe et al. |
| 4,025,617 A | 5/1977 | Green et al. |
| 4,025,627 A | 5/1977 | Green et al. |
| 4,025,653 A | 5/1977 | Green et al. |
| 4,026,945 A | 5/1977 | Green et al. |
| 4,027,008 A | 5/1977 | Sokol |
| 4,027,020 A | 5/1977 | Green et al. |
| 4,031,307 A | 6/1977 | DeMartino et al. |
| 4,070,533 A | 1/1978 | Papantoniou et al. |
| 4,075,136 A | 2/1978 | Schaper |
| 4,076,912 A | 2/1978 | Papantoniou et al. |
| 4,128,631 A | 12/1978 | Lundmark et al. |
| 4,129,711 A | 12/1978 | Viout et al. |
| 4,131,576 A | 12/1978 | Iovine et al. |
| 4,137,208 A | 1/1979 | Elliott |
| 4,157,388 A | 6/1979 | Christiansen |
| 4,165,367 A | 8/1979 | Chakrabarti |
| 4,172,887 A | 10/1979 | Vanlerberghe et al. |
| 4,217,914 A | 8/1980 | Jacquet et al. |
| 4,223,009 A | 9/1980 | Chakrabarti |
| 4,237,243 A | 12/1980 | Quack et al. |
| 4,277,581 A | 7/1981 | Vanlerberghe et al. |
| 4,282,203 A | 8/1981 | Jacquet et al. |
| 4,349,532 A | 9/1982 | Vanlerberghe et al. |
| 4,509,949 A | 4/1985 | Huang et al. |
| 4,591,610 A | 5/1986 | Grollier |
| 4,608,250 A | 8/1986 | Jacquet et al. |
| 4,673,568 A | 6/1987 | Grollier et al. |
| 4,693,935 A | 9/1987 | Mazurek |
| 4,702,906 A | 10/1987 | Jacquet et al. |
| 4,710,314 A | 12/1987 | Madrange et al. |

(Continued)

FOREIGN PATENT DOCUMENTS

AU 200039428 2/2001

(Continued)

OTHER PUBLICATIONS

"Encyclopedia of Chemical Technology", Kirk-Othmer, Third Edition, 1982, vol. 15, pp. 439-458.

(Continued)

*Primary Examiner*—Jyothsna Venkat
(74) *Attorney, Agent, or Firm*—Finnegan, Henderson, Farabow, Garrett & Dunner, L.L.P.

(57) ABSTRACT

A cosmetic composition for treating human keratin fibers, such as hair, comprising, in a cosmetically acceptable medium: (i) at least one reducing agent, and (ii) at least one particular aminosilicone.

The compositions can be used for bleaching and permanently reshaping human keratin fibers. Processes and devices for bleaching or permanently reshaping human keratin fibers using the composition.

44 Claims, No Drawings

U.S. PATENT DOCUMENTS

| | | | |
|---|---|---|---|
| 4,719,099 A | 1/1988 | Grollier et al. |
| 4,719,282 A | 1/1988 | Nadolsky et al. |
| 4,728,571 A | 3/1988 | Clemens et al. |
| 4,761,273 A | 8/1988 | Grollier et al. |
| 4,770,873 A | 9/1988 | Wolfram et al. |
| 4,839,166 A | 6/1989 | Grollier et al. |
| 4,957,732 A | 9/1990 | Grollier et al. |
| 4,972,037 A | 11/1990 | Garbe et al. |
| 4,996,059 A | 2/1991 | Grollier et al. |
| 5,009,880 A | 4/1991 | Grollier et al. |
| 5,057,311 A | 10/1991 | Kamegai et al. |
| 5,061,289 A | 10/1991 | Clausen et al. |
| 5,077,040 A | 12/1991 | Bergmann et al. |
| 5,085,860 A | 2/1992 | Junino et al. |
| 5,089,252 A | 2/1992 | Grollier et al. |
| 5,106,612 A | 4/1992 | Maignan et al. |
| 5,139,037 A | 8/1992 | Grollier et al. |
| 5,154,918 A | 10/1992 | Maignan et al. |
| 5,196,189 A | 3/1993 | Jacquet et al. |
| 5,210,324 A | 5/1993 | Farrar et al. |
| 5,340,367 A | 8/1994 | Schultz et al. |
| 5,344,464 A | 9/1994 | Madrange et al. |
| 5,380,340 A | 1/1995 | Neunhoeffer et al. |
| 5,466,878 A | 11/1995 | Junino et al. |
| 5,534,267 A | 7/1996 | Neunhoeffer et al. |
| 5,538,717 A | 7/1996 | De La Poterie |
| 5,583,257 A | 12/1996 | Junino et al. |
| 5,626,840 A | 5/1997 | Thomaides et al. |
| 5,663,366 A | 9/1997 | Neunhoeffer et al. |
| 5,708,151 A | 1/1998 | Mockli |
| 5,741,337 A | 4/1998 | Bone et al. |
| 5,756,076 A | 5/1998 | Cervantes et al. |
| 5,766,576 A | 6/1998 | Lowe et al. |
| 5,773,611 A | 6/1998 | Zysman et al. |
| 5,833,997 A | 11/1998 | Mahieu et al. |
| 5,925,341 A | 7/1999 | Cervantes et al. |
| 5,958,392 A | 9/1999 | Grollier et al. |
| 5,976,195 A | 11/1999 | De La Mettrie et al. |
| 6,010,541 A | 1/2000 | De La Mettrie |
| 6,071,504 A | 6/2000 | Kawai et al. |
| 6,099,592 A | 8/2000 | Vidal et al. |
| 6,099,593 A | 8/2000 | Terranova et al. |
| 6,143,286 A | 11/2000 | Bhambhani et al. |
| 6,177,090 B1 | 1/2001 | Dubief et al. |
| 6,179,881 B1 | 1/2001 | Henrion et al. |
| 6,214,326 B1 | 4/2001 | Dupuis |
| 6,254,646 B1 | 7/2001 | De La Mettrie et al. |
| 6,260,556 B1 | 7/2001 | Legrand et al. |
| 6,284,003 B1 | 9/2001 | Rose et al. |
| 6,319,959 B1 | 11/2001 | Mougin et al. |
| 6,372,876 B1 | 4/2002 | Kim et al. |
| 6,395,265 B1 | 5/2002 | Mougin et al. |
| 6,471,953 B1 | 10/2002 | N'Guyen et al. |
| 6,479,042 B1 | 11/2002 | Nguyen et al. |
| 6,506,373 B1 | 1/2003 | Dannecker et al. |
| 6,511,669 B1 | 1/2003 | Garnier et al. |
| 6,582,477 B1 * | 6/2003 | Plos ............................... 8/405 |
| 6,613,313 B1 | 9/2003 | Kimura |
| 6,770,271 B1 | 8/2004 | Mondet et al. |
| 6,824,764 B1 | 11/2004 | Devin-Baudoin et al. |
| 6,824,765 B1 | 11/2004 | Gawtrey et al. |
| 6,846,333 B1 * | 1/2005 | Legrand et al. ................ 8/405 |
| 6,916,467 B1 | 7/2005 | Devin-Baudoin et al. |
| 2002/0006389 A1 | 1/2002 | Restle et al. |
| 2002/0187117 A1 | 12/2002 | Devin-Baudoin et al. |

FOREIGN PATENT DOCUMENTS

| | | |
|---|---|---|
| EP | 0 227 994 | 9/1989 |
| EP | 0 342 834 | 11/1989 |
| EP | 0 486 135 | 5/1992 |
| EP | 0 412 707 | 2/1994 |
| EP | 0 582 152 | 2/1994 |
| EP | 0 646572 | 4/1995 |
| EP | 0 412 704 | 4/1999 |
| GB | 0 839 805 | 6/1960 |
| GB | 0 922 457 | 4/1963 |
| GB | 1 021 400 | 3/1966 |
| GB | 1 026 978 | 4/1966 |
| GB | 1 153 196 | 5/1969 |
| GB | 1 486 576 | 2/1977 |
| GB | 1 546 809 | 5/1979 |
| GB | 2 141 454 | 12/1984 |
| GB | 2 165 550 | 4/1986 |
| GB | 2 058 103 | 4/1991 |
| JP | 2001-10935 | 1/2001 |
| WO | WO 93/23446 | 11/1993 |
| WO | WO 94/07844 | 4/1994 |
| WO | WO 94/10131 | 5/1994 |
| WO | WO 94/24097 | 10/1994 |
| WO | WO 95/00578 | 1/1995 |
| WO | WO 95/01772 | 1/1995 |
| WO | WO 95/15144 | 6/1995 |
| WO | WO 95/16665 | 6/1995 |

OTHER PUBLICATIONS

"Encyclopedia of Chemical Technology", Kirk-Othmer, Third Edition, 1982, vol. 22, pp. 332-433.
"Encyclopedia of Chemical Technology", Kirk-Othmer, Third Edition, 1982, vol. 3, pp. 896-900.
"Industrial Gums—Polysaccharides and their Derivatives", edited by Roy L. Whistler, Second Edition, Academic Press.
"Polymers in Nature", E.A. MacGregor & C.T. Greenwood, John Wiley & Sons, Chapter 6, pp. 240-328, 1980.
"Volatile Silicone Fluids for Cosmetic Formulations", Cosmetics and Toiletries, vol. 91, Jan. 1976, pp. 27-32.
Copending U.S. Appl. No. 10/290,149, filed Nov. 8, 2002.
Copending U.S. Appl. No. 10/290,159, filed Nov. 8, 2002.
Copending U.S. Appl. No. 10/290,189, filed Nov. 8, 2002.
Copending U.S. Appl. No. 10/290,192, filed Nov. 8, 2002.
Copending U.S. Appl. No. 10/290,226, filed Nov. 8, 2002.
Copending U.S. Appl. No. 10/290,341, filed Nov. 8, 2002.
Copending U.S. Appl. No. 10/290,342, filed Nov. 8, 2002.
Copending U.S. Appl. No. 10/290,343, filed Nov. 8, 2002.
Copending U.S. Appl. No. 10/290,345, filed Nov. 8, 2002.
Copending U.S. Appl. No. 10/290,348, filed Nov. 8, 2002.
Copending U.S. Appl. No. 10/290,372, filed Nov. 8, 2002.
Copending U.S. Appl. No. 10/290,409, filed Nov. 8, 2002.
Copending U.S. Appl. No. 11/158,014, filed Jun. 22, 2005.
English language Derwent Abstract of DE 197 54 053, Jun. 10, 1999.
English language Derwent Abstract of DE 42 29 922, Mar. 10, 1994.
English language Derwent Abstract of DE 44 02 929, Jun. 22, 1995.
English language Derwent Abstract of DE 44 20 736, Aug. 10, 1995.
English language Derwent Abstract of DE 44 24 530, Jan. 18, 1996.
English language Derwent Abstract of DE 44 24 533, Jan. 18, 1996.
English language Derwent Abstract of EP 0 080 976, Jun. 8, 1983.
English language Derwent Abstract of EP 0 122 324, Oct. 24, 1984.
English language Derwent Abstract of EP 0 225 261, Jun. 10, 1987.
English language Derwent Abstract of EP 0 368 763, May 16, 1990.
English language Derwent Abstract of EP 0 765 655, Apr. 2, 1987.
English language Derwent Abstract of FR 2 679 448, Jan. 29, 1993.
English language Derwent Abstract of FR 2 679 558, Jan. 29, 1993.
English language Derwent Abstract of JP 2001-10936, Jan. 16, 2001.
English language Derwent Abstract of JP-2-250814, Oct. 8, 1990.
English language Derwent Abstract of JP 4-154713, May 27, 1992.
English language Derwent Abstract of JP 8-157340, Jun. 18, 1996.
English language Derwent Abstract of JP 9-151120, Jun. 10, 1997.
English language JAPIO Abstract of JP 2-019576, Jan. 23, 1990.
English language JAPIO Abstract of JP 9-110659, Apr. 28, 1997.
French Search Report for FR 0 114 468, dated Aug. 8, 2002.
French Search Report for FR 0 114 469, dated Aug. 22, 2002.

French Search Report for FR 0 114 470, dated Sep. 18, 2002.
French Search Report for FR 0 114 472, dated Aug. 30, 2002.
French Search Report for FR 0 114 473, dated Sep. 16, 2002.
French Search Report for FR 0 114 474, dated Aug. 8, 2002.
French Search Report for FR 0 114 476, dated Sep. 20, 2002.
French Search Report for FR 0 114 477, dated Sep. 20, 2002.
French Search Report for FR 0 114 478, dated Sep. 18, 2002.
French Search Report for FR 0 114 479, dated Sep. 16, 2002.
French Search Report for FR 0 114 480, dated Aug. 9, 2002.
French Search Report for FR 0 114 481, dated Sep. 4, 2002.
French Search Report for FR 0 114 482, dated Aug. 28, 2002.
French Search Report for FR 0 114 484, dated Sep. 4, 2002.
French Search Report for FR 0 114 485, dated Aug. 29, 2002.
French Search Report for FR 0 114 486, dated Sep. 23, 2002.
P.D. Dorgan "Waxes in Cosmetics", Drug and Cosmetic Industry, Dec. 1983, pp. 30-33.
Porter, M.R., Handbook of Surfactants 116-178 (Blackie & Son 1991).
English language Patent Abstract of Japan of JP 2001-10935, Jan. 16, 2001.
Office Action in co-pending U.S. Appl. No. 10/290,149, dated Apr. 30, 2004 (Ex. Elhilo).
Office Action in co-pending U.S. Appl. No. 10/290,149, dated Nov. 4, 2004 (Ex. Elhilo).
Office Action in co-pending U.S. Appl. No. 10/290,159, dated Dec. 27, 2004 (Ex. Elhilo).
Office Action in co-pending U.S. Appl. No. 10/290,159, dated May 3, 2004 (Ex. Elhilo).
Office Action in co-pending U.S. Appl. No. 10/290,189, dated Feb. 16, 2006 (Ex. Venkat).
Office Action in co-pending U.S. Appl. No. 10/290,192, dated Jan. 11, 2006 (Ex. Venkat).
Office Action in co-pending U.S. Appl. No. 10/290,341, dated Jan. 11, 2006 (Ex. Venkat).
Office Action in co-pending U.S. Appl. No. 10/290,342, dated Jan. 25, 2006 (Ex. Venkat).
Office Action in co-pending U.S. Appl. No. 10/290,343, dated Jan. 25, 2006 (Ex. Venkat).
Office Action in co-pending U.S. Appl. No. 10/290,345, dated Feb. 9, 2006 (Ex. Venkat).
Office Action in co-pending U.S. Appl. No. 10/290,372, dated Jan. 10, 2006 (Ex. Venkat).

* cited by examiner

REDUCING COMPOSITION FOR TREATING KERATIN FIBRES, COMPRISING A PARTICULAR AMINOSILICONE This disclosure relates to a novel composition for treating human keratin fibres, such as hair, comprising, in a cosmetically acceptable medium, (i) at least one reducing agent, and (ii) at least one aminosilicone, as defined herein.

The disclosure also relates to uses of the composition for bleaching and/or permanently reshaping human keratin fibres, such as hair. The disclosure further relates to bleaching and/or permanent-reshaping processes and/or devices for using the composition.

It is a well-known practice to bleach keratin fibres, for example, human keratin fibres, such as hair, with bleaching compositions containing one or more oxidizing agents. Among the oxidizing agents conventionally used, mention may be made of hydrogen peroxide or compounds capable of producing hydrogen peroxide by hydrolysis, such as urea peroxide or persalts such as perborates, percarbonates and persulphates, such as, for example, hydrogen peroxide and persulphates.

It is also a well-known practice to bleach human keratin fibres, such as hair. For example, hair may be artificially dyed with exogenous colorants, using reducing agents such as ascorbic acid or thiols, for example, cysteine.

It is also a well-known practice to permanently reshape human keratin fibres, such as hair. Such reshaping may be done by, for example, applying compositions containing one or more reducing agents to the hair. For example, the hair may be placed under tension beforehand using mechanical devices such as curlers. The hair is reduced and then reoxidized in the desired shape, usually after rinsing. Not only may atmospheric oxygen be used, but also an oxidizing agent that may be chosen from aqueous hydrogen peroxide solution and alkali metal bromates may be used.

The reducing agents that may be used for the permanent reshaping of hair include thiols, such as thioglycolic acid, its salts and its esters, thiolactic acid and its salts, cysteine or cysteamine, and sulphites.

Compositions for bleaching hair using reducing agents may be in the form of ready-to-use compositions comprising anhydrous products (e.g., powders or creams) containing the reducing agent(s), which may be mixed at the time of use with an aqueous composition optionally containing a pH agent. Bleaching compositions may also be in the form of ready-to-use aqueous compositions containing the reducing agent(s) at the appropriate pH.

Reducing compositions for permanently reshaping the hair may be in the form of ready-to-use aqueous compositions or in the form of liquid or pulverulent anhydrous compositions, which are mixed at the time of use with an aqueous composition at the appropriate pH.

Moreover, it is well-known that the treatment involved in the permanent reshaping of the hair and the treatment involved in bleaching may be aggressive. These treatments may lead to poor cosmetic properties of the hair, such as difficulty in disentangling, an unpleasant feel, or coarse, dull hair, or hair charged with static electricity, and to degradation of the fibres.

After considerable research, the inventors have discovered that by using at least one aminosilicone defined below in a reducing composition for bleaching and/or permanently reshaping human keratin fibres, such as hair, at least one of these drawbacks may be overcome, with conditioning and remanent effects that can be superior to those of the systems previously used, without, however, impairing at least one of the intensity and homogeneity of the bleaching or permanent-reshaping results.

Thus, the condition of the human keratin fibres may be improved, and the fibres can maintain their soft feel, their ease of disentangling, and their sheen after shampooing several times.

The phrase "improvement in the condition of the fibre" means, for example, a reduction in the porosity or the alkaline solubility of the fibre and an improvement in at least one cosmetic property such as, for example, the smoothness, softness, and ease of disentangling and styling.

This effect can be remanent, i.e., long-lasting.

The porosity is measured by fixing, at 37° C. and at pH 10, for 2 minutes, 2-nitro-para-phenylenediamine at 0.25% in an ethanol/pH 10 buffer mixture (10/90 volume ratio).

The alkaline solubility corresponds to the loss of mass of a sample of 100 mg of keratin fibres under the action of decinormal sodium hydroxide for 30 minutes at 65° C.

These discoveries form at least a portion of the basis for at least one embodiment disclosed herein.

A new embodiment relates to a cosmetic composition for treating human keratin fibres, such as hair, comprising, in a cosmetically acceptable medium:
(i) at least one reducing agent, and
(ii) at least one aminosilicone chosen from formulae (I) and (II) described below.

A new embodiment relates to a ready-to-use composition for bleaching or permanently reshaping human keratin fibres, such as hair, comprising at least one reducing agent in a medium that is suitable for bleaching or permanent reshaping, and at least one aminosilicone chosen from formulae (I) and (II), as defined herein.

The phrase "ready-to-use composition" means, for example, the composition is applied in unmodified form to the human keratin fibres, such as hair, e.g., the composition may be stored in unmodified form before use or may result from the extemporaneous mixing of at least two compositions.

When the ready-to-use composition results from the extemporaneous mixing of at least two compositions, the at least one aminosilicone, defined herein, is present in one or more of the pre-mixed compositions.

The at least one aminosilicone defined herein may be present in an anhydrous composition in the form of a powder, for example, pulverulent powder, or in the form of a cream and/or in one or more aqueous compositions.

The at least one aminosilicone defined herein may also be present in at least one aqueous composition, which may be mixed at the time of use with a composition that can be either aqueous or anhydrous, in the form of a powder or a cream, and comprising at least one reducing agent.

The composition may be a single composition comprising at least one reducing agent and at least one aminosilicone, as defined herein.

The at least one aminosilicone defined herein can be used in an anhydrous composition further comprising at least one reducing agent, the composition, for example, being intended to be diluted before being applied to the fibres.

The disclosure also relates to a bleaching process and/or a permanent-reshaping process for human keratin fibres, such as hair, using the ready-to-use bleaching or permanent-reshaping composition as described herein. The application of the composition may be followed, in the case of permanent reshaping, by the application, optionally after rinsing, of an oxidizing composition.

The disclosure relates further to bleaching devices or packaging "kits" comprising a ready-to-use composition.

In an embodiment, a multi-compartment device or kit may comprise at least one first compartment comprising at least one anhydrous powder or at least one anhydrous cream or an aqueous composition, and at least one second compartment comprising an aqueous composition, at least one of the compartments comprising at least one reducing agent and at least one of the compartments comprising at least one aminosilicone chosen from formulae (I) and (II).

At least one other characteristic, aspect, subject and advantage of embodiments disclosed herein will emerge even more clearly on reading the description and the examples that follow without, however, exhibiting a limiting character.

Aminosilicones

The at least one aminosilicone is chosen from formulae (I) and (II):

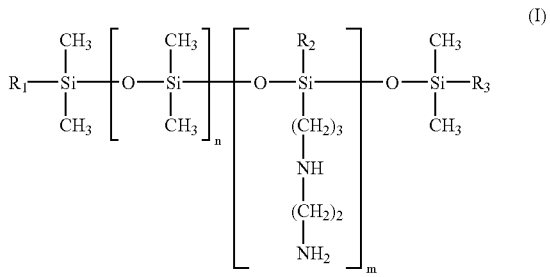

(I)

wherein:
m and n are chosen from numbers such that the sum (n+m) ranges from 1 to 1000 and, for example, from 50 to 250 and, in yet another example, from 100 to 200;
n ranges from 0 to 999 and, for example from 49 to 249 and further, for example, from 125 to 175, and m ranges from 1 to 1000, for example, from 1 to 10 and further, for example, from 1 to 5;
$R_1$, $R_2$ and $R_3$, which may be identical or different, are chosen from a hydroxyl radical and $C_1$–$C_4$ alkoxy radicals, wherein at least one of the radicals $R_1$ to $R_3$ are chosen from alkoxy radicals.

For example, the alkoxy radical may be a methoxy radical.

The hydroxyl/alkoxy molar ratio may range from 0.2:1 to 0.4:1, for example, from 0.25:1 to 0.35:1 and further, for example, is 0.3:1.

The at least one aminosilicone of formula (I) may have a weight-average molecular mass ranging from 2000 to 1 000 000, for example from 3500 to 200 000.

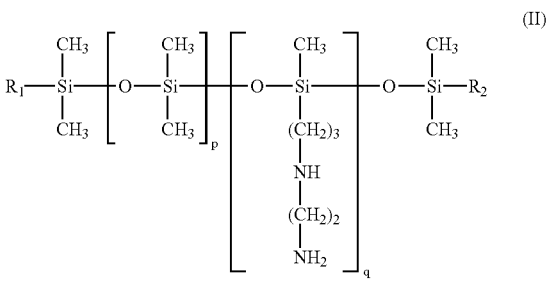

(II)

wherein:
p and q are chosen from numbers such that the sum (p+q) ranges from 1 to 1000, and for example from 50 to 350 and further, for example, from 150 to 250;
p is chosen from a number ranging from 0 to 999, for example from 49 to 349 and further, for example, from 159 to 239, and q is chosen from a number ranging from 1 to 1000, for example from 1 to 10 and further, for example, from 1 to 5;
$R_1$ and $R_2$, which are different, are chosen from a hydroxyl radical and $C_1$–$C_4$ alkoxy radical, wherein at least one of the radicals $R_1$ and $R_2$ is chosen from alkoxy radicals.

For example, the alkoxy radical may be a methoxy radical.

The hydroxyl/alkoxy molar ratio may range, for example, from 1:0.8 to 1:1.1, and further, for example, from 1:0.9 to 1:1 and, for yet another example, may be 1:0.95.

The at least one aminosilicone of formula (II) may have a weight-average molecular mass ranging, for example, from 2000 to 200 000, for example from 5000 to 100 000 and further, for example, from 10 000 to 50 000.

The weight-average molecular mass of the at least one aminosilicone may be measured by Gel Permeation Chromatography (GPC) at room temperature, as a polystyrene equivalent. The columns used are styragel μ columns. The eluent is THF, and the flow rate is 1 ml/minute. 200 μl of a solution at 0.5% by weight of silicone in THF are injected. The detection is performed by refractometry and UV-metry.

An embodiment of the comprising at least one aminosilicone of formula (I) or (II) may include at least one additional aminosilicone, whose formula is different from formulae (I) and (II).

A product comprising at least one aminosilicone of structure (I) is sold, for example, by the company Wacker under the name Belsil ADM 652®.

Products comprising at least one aminosilicone of structure (II) are sold, for example, by the company Wacker under the names Fluid WR 1300® and Belsil ADM 6057®.

When the at least one aminosilicone is used, one embodiment involves using the at least one aminosilicone in the form of an oil-in-water emulsion. The oil-in-water emulsion may comprise at least one surfactant. The at least one surfactant may be of any nature, for example cationic and/or nonionic.

The at least one aminosilicone particles (i.e., the mean particle size of the at least one aminosilicone) in the emulsion may have a mean size ranging from 3 to 500 nanometres. Such particle sizes are measured with a laser granulometer.

For example, for the at least one aminosilicone of formula (II), particles in microemulsions may range in size from 5 to 60 nanometres and, for example, from 10 to 50 nanometres. One skilled in the art can measure such sizes using art-recognized methods.

A microemulsion of the at least one aminosilicone of formula (II), sold under the name Finish CT 96 E® or SLM 28020® by the company Wacker, may be used.

The at least one aminosilicone chosen from formulae (I) and (II) may be chosen such that the contact angle with water of a hair treated with a composition comprising 2% AM (active materials) of the at least one aminosilicone ranges from 90 to 180°, for example from 90 to 130°. As used herein, a range "from x to y" includes within the range the endpoints x and y.

The composition comprising the at least one aminosilicone chosen from formula (I) and (II) may be chosen such that the contact angle of a hair treated with the composition ranges from 90 to 180°, for example, from 90 to 130°.

The contact angle measurement may be based on immersing a hair in distilled water. The measurement is derived from evaluating the force exerted by the water on the hair during its immersion in distilled water and the force exerted during its removal. The forces are directly linked to the contact angle θ between the water and the surface of the hair. The hair is hydrophilic when the angle θ is from 0 to less than 90°, and hydrophobic when the angle is from 90° to 180°.

The test is carried out with locks of natural hair that have been bleached under the same conditions and then washed.

Each 1 gram lock is placed in a crystallizing dish 75 mm in diameter and covered uniformly with 5 ml of the test formulation. The lock is left for 15 minutes at room temperature and then rinsed for 30 seconds. The drained lock is left in the open air until it is completely dry.

For each evaluation, 10 hairs that have undergone the same treatment are analysed. Each sample, attached to a precision microbalance, is immersed via its end in a container filled with distilled water. This DCA balance ("Dynamic Contact Angle Analyser"), from the company Cahn Instruments, allows the force (F) exerted by the water on the hair to be measured.

In parallel, the perimeter (P) of each hair is measured by means of observation by microscope.

The mean wettability force on 10 hairs and the cross section of the analysed hairs make it possible to obtain the contact angle of the hair on the water, according to the formula:

$$F = P \ast \Gamma l v \ast \cos \theta$$

where F is the wettability force expressed in newtons, P is the perimeter of the hair in metres, Γlv is the liquid/water vapour interface tension in $J/m^2$, and θ is the contact angle.

For example, the product SLM 28020® from Wacker at 12% in water (i.e. 2% aminosilicone) gives a contact angle of 93° according to the test indicated above.

The at least one aminosilicone chosen from formula (I) and (II), for example, may be used in the reducing composition in an amount ranging from 0.01% to 20% by weight relative to the total weight of the composition. For example, this amount ranges from 0.1% to 15% by weight and, and further, for example, from 0.5% to 10% by weight.

Reducing Agents

The at least one reducing agent that may be used may be chosen from the group formed by thiols, such as cysteine, thioglycolic acid, thiolactic acid, salts thereof and esters thereof, cysteamine and its salts, and sulphites.

According to an embodiment, ascorbic acid, its salts and its esters, erythorbic acid, its salts and its esters, and sulphinates, for example sodium hydroxymethanesulphinate, may also be used.

The at least one reducing agent is used in a composition in concentrations ranging from 0.1% to 30%, for example from 0.5% to 20% by weight, relative to the total weight of the composition.

Ingredients

The compositions may also comprise agents for adjusting the rheology, such as those chosen from cellulosic thickeners (hydroxyethylcellulose, hydroxypropylcellulose, carboxymethylcellulose, etc.), guar gum and its derivatives (hydroxypropyl guar, etc.), gums of microbial origin (xanthan gum, scleroglucan gum, etc.), and synthetic thickeners such as crosslinked homopolymers of acrylic acid or of acrylamidopropanesulphonic acid.

A composition may also comprise at least one ionic or nonionic associative polymer chosen, for example, from the polymers sold under the names Pemulen® TR1 or TR2 by the company Goodrich, Salcare SC 90® by the company Allied Colloids, Aculyne® 22, 28, 33, 44 or 46 by the company Rohm & Haas, and Elfacos® T210 and T212 by the company Akzo, in a proportion ranging from 0.01% to 10% by weight relative to the total weight of the composition.

The composition may also comprise at least one cationic or amphoteric polymer that is well-known in the art of dyeing human keratin fibres, such as hair, in an amount ranging from 0.01% to 10% by weight, for example from 0.05% to 5% and further, for example, from 0.1% to 3%, relative to the total weight of the composition.

Cationic Polymers

The expression "cationic polymer" means, for example, any polymer comprising cationic groups and/or groups which may be ionized into cationic groups.

The at least one cationic polymer may be chosen from any of those already known by those skilled in the art as improving at least one of the cosmetic properties of the hair, for example, those described in European patent application EP-A-337 354, and in French Patent Nos. FR-2 270 846, 2 383 660, 2 598 611, 2 470 596 and 2 519 863.

The at least one cationic polymer may be chosen from those comprising units comprising at least one amine group chosen from primary, secondary, tertiary and quaternary amine groups, which may either form part of the main polymer chain or may be borne by a side substituent directly attached to the main polymer chain.

The at least one cationic polymer used may have a number-average molecular mass ranging from 500 to $5 \times 10^6$, for example from $10^3$ to $3 \times 10^6$.

The at least one cationic polymer may be chosen, for example, from polymers of polyamine, polymers of polyamino amide and polymers of polyquaternary ammonium. These products are well-known in the art.

The polymers of polyamine, polymers of polyamino amide, and polymers of polyquaternary ammonium that may be used are described, for example, in French Patent Nos. 2 505 348 and 2 542 997. Among the cationic polymers, mention may be made of:

(1) homopolymers or copolymers derived from acrylic or methacrylic esters or amides and comprising at least one of unit chosen from units of formula (I), (II), (III) and (IV) below:

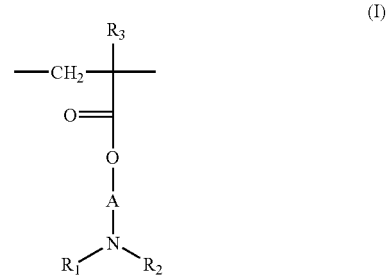

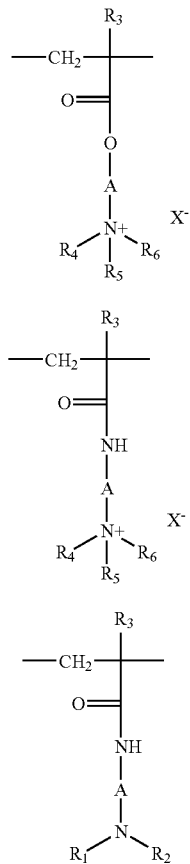

wherein:
R$_3$, which may be identical or different, is chosen from a hydrogen atom and a CH$_3$ radical;
A, which may be identical or different, is chosen from linear and branched alkyl groups of 1 to 6 carbon atoms, such as 2 or 3 carbon atoms, and hydroxyalkyl groups of 1 to 4 carbon atoms;
R$_4$, R$_5$ and R$_6$, which may be identical or different, are chosen from alkyl groups comprising from 1 to 18 carbon atoms, for example, an alkyl group comprising from 1 to 6 carbon atoms, and benzyl radicals;
R$_1$ and R$_2$, which may be identical or different, are chosen from hydrogen and alkyl groups comprising from 1 to 6 carbon atoms, for example, methyl and ethyl groups;
X$^-$0 is chosen from anions derived from inorganic and organic acids, such as a methosulphate anion, and halides, such as chloride and bromide.

The polymers of family (1) can also comprise at least one unit derived from comonomers that may be chosen from the family of acrylamides, methacrylamides, diacetoneacrylamides, acrylamides and methacrylamides substituted on the nitrogen with at least one group chosen from lower (C$_1$–C$_4$) alkyls, acrylic acids, methacrylic esters, and vinyllactams, such as vinylpyrrolidone, vinylcaprolactam, and vinyl esters.

Thus, among these polymers of family (1), mention may be made of:
the copolymers of acrylamide and of dimethylaminoethyl methacrylate quaternized with dimethyl sulphate or with a dimethyl halide, such as the product sold under the name Hercofloc™ by the company Hercules,
copolymers of acrylamide and of methacryloyloxyethyltrimethylammonium chloride described, for example, in patent application EP-A-080 976 and sold under the name Bina Quat P 100 by the company Ciba Geigy,
the copolymer of acrylamide and of methacryloyloxyethyltrimethylammonium methosulphate sold under the name Reten by the company Hercules,
quaternized or non-quaternized vinylpyrrolidone/dialkylaminoalkyl acrylate or methacrylate copolymers, such as the products sold under the name "Gafquat" by the company ISP, for example, "Gafquat 734" or "Gafquat 755", or the products known as "Copolymer 845, 958 and 937." These polymers are described, for example, in French Patent Nos. 2 077 143 and 2 393 573,
dimethylaminoethyl methacrylate/vinylcaprolactam/vinylpyrrolidone terpolymers, such as the product sold under the name "Gaffix VC 713" by the company ISP,
vinylpyrrolidone/methacrylamidopropyldimethylamine copolymers sold, for example, under the name "Styleze CC 10" by ISP, and
quaternized vinylpyrrolidone/dimethylaminopropylmethacrylamide copolymers such as the product sold under the name "Gafquat HS 100" by the company ISP.

(2) The cellulose ether derivatives comprising quaternary ammonium groups, described in French Patent No. 1 492 597, and the polymers sold under the names "JR" (JR 400, JR 125 and JR 30M) or "LR" (LR 400, or LR 30M) by the company Union Carbide Corporation. These polymers are also defined in the CTFA dictionary as quaternary ammoniums of hydroxyethylcellulose which has reacted with an epoxide substituted with a trimethylammonium group.

(3) The cationic cellulose derivatives such as cellulose copolymers or cellulose derivatives grafted with a water-soluble monomer of quaternary ammonium, described in U.S. Pat. No. 4,131,576, such as hydroxyalkylcelluloses, for instance, hydroxymethyl-celluloses, hydroxyethylcelluloses or hydroxypropylcelluloses grafted, for example, with a salt chosen from methacryloylethyltrimethylammonium salts, methacrylamidopropyltrimethylammonium salts and dimethyldiallylammonium salts.

The commercial products corresponding to this definition are, for example, the products sold under the names "Celquat L 200" and "Celquat H 100" by the company National Starch.

(4) The cationic polysaccharides described in U.S. Pat. Nos. 3,589,578 and 4,031,307, such as guar gums comprising cationic trialkylammonium groups. Guar gums modified with a salt (e.g. chloride) of 2,3-epoxypropyltrimethylammonium may also be used.

Such products are sold, for example, under the trade names Jaguar C 13 S, Jaguar C 15, Jaguar C 17 or Jaguar C162 by the company Meyhall.

(5) Polymers comprising piperazinyl units and divalent alkylene or hydroxyalkylene radicals comprising straight or branched chains, optionally interrupted by at least one atom chosen from oxygen, sulphur and nitrogen atoms or by at least one aromatic or heterocyclic ring, and also at least one of the oxidation and/or quaternization products of these polymers. Such polymers are described, for example, in French Patent Nos. 2 162 025 and 2 280 361.

(6) Water-soluble polyamino amides prepared, for example, by polycondensation of an acidic compound with a polyamine; these polyamino amides can be crosslinked with an epihalohydrin, a diepoxide, a dianhydride, an unsaturated dianhydride, a bis-unsaturated derivative, a bis-halohydrin, a bis-azetidinium, a bis-haloacyldiamine, a bis-alkyl halide or with an oligomer resulting from the reaction of a difunctional compound which is reactive with a bis-halohydrin, a bis-azetidinium, a bis-haloacyldiamine, a bis-alkyl halide, an epihalohydrin, a diepoxide or a bis-unsaturated derivative. The crosslinking agent can be used in proportions ranging from 0.025 to 0.35 mol per amine group of the polyamino amide. These polyamino amides can be alkylated or, if they comprise at least one tertiary amine function, they can be quaternized. Such polymers are described, for example, in French Patent Nos. 2 252 840 and 2 368 508.

(7) The polyamino amide derivatives resulting from the condensation of polyalkylene polyamines with polycarboxylic acids followed by alkylation with difunctional agents. Mention may be made, for example, of adipic acid/dialkylaminohydroxyalkyldialkylenetriamine polymers in which the alkyl radical comprises from 1 to 4 carbon atoms and, for example, may be chosen from methyl, ethyl, and propyl groups. Such polymers are described, for example, in French Patent No. 1 583 363.

Among these derivatives, mention may be made, for example, of the adipic acid/dimethylaminohydroxypropyl/diethylenetriamine polymers sold under the name "Cartaretine F, F4 or F8" by the company Sandoz.

(8) The polymers obtained by reaction of a polyalkylene polyamine comprising two primary amine groups and at least one secondary amine group with a dicarboxylic acid chosen from diglycolic acids and saturated aliphatic dicarboxylic acids comprising from 3 to 8 carbon atoms. The molar ratio between the polyalkylene polyamine and the dicarboxylic acid may range, for example, from 0.8:1 to 1.4:1; the polyamino amide resulting therefrom may be reacted with epichlorohydrin in a molar ratio of epichlorohydrin relative to the secondary amine group of the polyamino amide ranging from 0.5:1 to 1.8:1. Such polymers are described, for example, in U.S. Pat. Nos. 3,227,615 and 2,961,347.

Other non-limiting examples of such derivatives include the adipic acid/epoxypropyl/diethylenetriamine copolymers sold, for example, under the name "Hercosett 57" by the company Hercules Inc. or under the name "PD 170" or "Delsette 101" by the company Hercules Inc.

(9) Cyclopolymers of alkyldiallylamine or of dialkyldiallylammonium, such as the homopolymers or copolymers comprising, as main constituent of the chain, at least one unit corresponding to formula (V) or (VI):

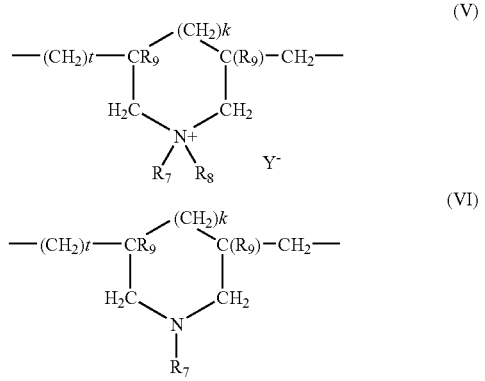

wherein k and t are equal to 0 or 1, the sum k+t being equal to 1; $R_9$ is chosen from a hydrogen atom and a methyl radical; $R_7$ and $R_8$, which may be identical or different, are chosen from alkyl groups comprising from 1 to 8 carbon atoms, hydroxyalkyl groups in which the alkyl group comprises, for example, 1 to 5 carbon atoms, and lower $C_1$–$C_4$ amidoalkyl groups, or $R_7$ and $R_8$ can be chosen from, together with the nitrogen atom to which they are attached, heterocyclic groups such as piperidyl or morpholinyl; or $R_7$ and $R_8$, which may be identical or different, may be chosen from alkyl groups comprising from 1 to 4 carbon atoms; $Y^-$ is an anion chosen from bromide, chloride, acetate, borate, citrate, tartrate, bisulphate, bisulphite, sulphate and phosphate. These polymers are described, for example, in French Patent No. 2 080 759 and in its Certificate of Addition 2 190 406.

Among the polymers defined above, mention may be made, for example, of the dimethyldiallylammonium chloride homopolymer sold under the name "Merquat 100" by the company Calgon (and its homologues of low weight-average molecular mass) and copolymers of diallyldimethylammonium chloride and of acrylamide, sold under the name "Merquat 550."

(10) The quaternary diammonium polymer comprising repeating units corresponding to the formula (VII):

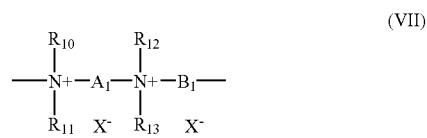

wherein:

$R_{10}$, $R_{11}$, $R_{12}$ and $R_{13}$, which may be identical or different, are chosen from aliphatic radicals, alicyclic radicals and arylaliphatic radicals comprising from 1 to 20 carbon atoms, and from lower hydroxyalkylaliphatic radicals, or $R_{10}$, $R_{11}$, $R_{12}$ and $R_{13}$, together or separately, constitute, with the nitrogen atoms to which they are attached, heterocycles optionally comprising a second heteroatom other than nitrogen, or $R_{10}$, $R_{11}$, $R_{12}$ and $R_{13}$, which may be identical or different, are chosen from linear and branched $C_1$–$C_6$ alkyl radicals substituted with at least one group chosen from nitrile, ester, acyl and amide groups and groups of formulae —CO—O—$R_{14}$—D and —CO—NH—$R_{14}$—D wherein $R_{14}$ is chosen from alkylene groups and D is chosen from quaternary ammonium groups;

$A_1$ and $B_1$, which may be identical or different, are chosen from linear and branched saturated and unsaturated polymethylene groups comprising from 2 to 20 carbon atoms. The polymethylene groups may comprise, linked to or intercalated in the main chain, at least one entity chosen from aromatic rings, oxygen or sulphur atoms and sulphoxide, sulphone, disulphide, amino, alkylamino, hydroxyl, quaternary ammonium, ureido, amide and ester groups, and $X^-$ is an anion chosen from anions derived from mineral and organic acids;

$A_1$, $R_{10}$ and $R_{12}$ may optionally form, with the two nitrogen atoms to which they are attached, a piperazine ring. In addition, if $A_1$ is a radical chosen from linear and branched, saturated and unsaturated alkylenes and hydroxyalkylene radicals, $B_1$ can be chosen from a group —$(CH_2)_n$—CO—D—OC—$(CH_2)_n$— wherein n ranges from 1 to 100, such as from 1 and 50. D is chosen from:

a) a glycol residue of formula: —O—Z—O—, wherein Z is chosen from linear and branched hydrocarbon-based radicals and a group corresponding to one of the following formulae:

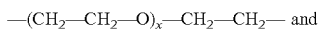

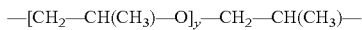

wherein x and y, which may be identical or different, are each an integer ranging from 1 to 4, representing a defined and unique degree of polymerization or any number ranging from 1 to 4 representing an average degree of polymerization;

b) a bis-secondary diamine residue such as a piperazine derivative;

c) a bis-primary diamine residue of formula: —NH—Y—NH—, wherein Y is chosen from linear and branched hydrocarbon-based radicals, and the divalent radical

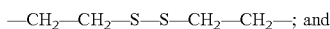

d) a ureylene group of formula: —NH—CO—NH—;

In one embodiment, $X^-$ is an anion such as chloride or bromide.

These polymers may have a number-average molecular mass ranging from 1000 to 100 000.

These polymers are described, for example, in French Patent Nos. 2 320 330, 2 270 846, 2 316 271, 2 336 434 and 2 413 907 and U.S. Pat. Nos. 2,273,780, 2,375,853, 2,388,614, 2,454,547, 3,206,462, 2,261,002, 2,271,378, 3,874,870, 4,001,432, 3,929,990, 3,966 904, 4,005,193, 4,025,617, 4,025,627, 4,025,653, 4,026,945 and 4,027,020.

Furthermore, the polymers that comprise repeating units corresponding to formula (VIII) below can be used:

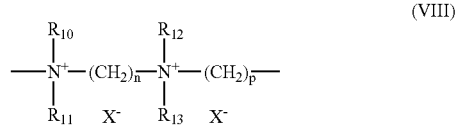

(VIII)

wherein $R_{10}$, $R_{11}$, $R_{12}$ and $R_{13}$, which may be identical or different, are chosen from alkyl and hydroxyalkyl radicals comprising from 1 to 4 carbon atoms, n and p, which may be identical or different, are integers ranging from 2 to 20, and $X^-$ is an anion chosen from anions derived from mineral and organic acids, for example, where $R_{10}$, $R_{11}$, $R_{12}$ and $R_{13}$ are each a methyl radical, n=3, p=6, and X=Cl, known as hexadimethine chloride, according to the INCI (CFTA) nomenclature.

(11) Polyquaternary ammonium polymers comprising repeating units of formula (IX):

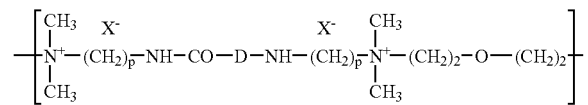

(IX)

wherein p is an integer ranging from 1 to 6, D may be nothing or may represent a group —$(CH_2)_r$—CO— in which r may be an integer ranging from 4 to 7, and $X^-$ is an anion.

Such polymers may be prepared according to the processes described in U.S. Pat. Nos. 4,157,388, 4,702,906 and 4,719,282. They are also described, for example, in European patent application EP-A-122 324.

Among these polymers, mention may be made, for example, of "Mirapol A 15", "Mirapol AD1", "Mirapol AZ1" and "Mirapol 175" sold by the company Miranol.

(12) Quaternary polymers of vinylpyrrolidone and of vinylimidazole, such as the products sold under the names Luviquat FC 905, FC 550 and FC 370 by the company BASF.

(13) Polyamines such as Polyquart H sold by Henkel, under the reference name "Polyethylene glycol (15) tallow polyamine" in the CTFA dictionary.

(14) Crosslinked methacryloyloxy($C_1$–$C_4$)alkyltri($C_1$–$C_4$)alkylammonium salt polymers such as the polymers obtained by homopolymerization of dimethylaminoethyl methacrylate quaternized with methyl chloride, or by copolymerization of acrylamide with dimethylaminoethyl methacrylate quaternized with methyl chloride, the homo- or copolymerization being followed by crosslinking with a compound comprising olefinic unsaturation, such as methylenebisacrylamide. A crosslinked acrylamide/methacryloyloxyethyltrimethylammonium chloride copolymer (20/80 by weight) in the form of a dispersion comprising 50% by weight of the copolymer in mineral oil can be used. This dispersion is sold under the name "Salcare® 92" by the company Allied Colloids. In another embodiment, a crosslinked methacryloyloxyethyltrimethylammonium chloride homopolymer comprising about 50% by weight of the homopolymer in mineral oil or in a liquid ester can also be used. These dispersions are sold under the names "Salcare® 95" and "Salcare® 96" by the company Allied Colloids.

Other cationic polymers, which can be used, are chosen from polyalkyleneimines, for example, polyethyleneimines, polymers comprising vinylpyridine and vinylpyridinium units, condensates of polyamines and of epichlorohydrin, quaternary polyureylenes and chitin derivatives.

The at least one cationic polymer may be chosen, for example, from polymers of families (1), (9), (10), (11) and (14) and polymers comprising repeating units chosen from formulae (W) and (U):

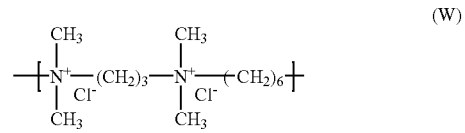

(W)

and, for example, those polymers comprising repeating units of formula (W) whose weight-average molar mass, determined by gel permeation chromatography, ranges from 9500 to 9900;

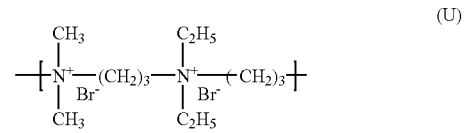

(U)

and, for example, those polymers comprising repeating units of formula (U) whose weight-average molar mass, determined by gel permeation chromatography, is about 1200.

The concentration of the at least one cationic polymer other than cationic poly(vinyllactam) in the composition may range, for example, from 0.01% to 10% by weight relative to the total weight of the composition, for example from 0.05% to 5% by weight and further, for example, from 0.1% to 3% by weight relative to the total weight of the composition.

Amphoteric Polymers

The amphoteric polymers, which may be used, may be chosen from polymers comprising units K and M randomly distributed in the polymer chain, wherein K is a unit derived from a monomer comprising at least one basic nitrogen atom and M is a unit derived from an acidic monomer comprising at least one carboxylic or sulphonic group, or K and M may be chosen from groups derived from zwitterionic carboxybetaine or sulphobetaine monomers.

K and M may also be chosen from a cationic polymer chain comprising at least one group chosen from primary, secondary, tertiary and quaternary amine groups, wherein at least one of the amine groups bears a carboxylic or sulphonic group linked via a hydrocarbon-based radical, or K and M can form part of a chain of a polymer comprising an α,β-dicarboxylic ethylene unit in which one of the carboxylic groups has been made to react with a polyamine comprising at least one amine chosen from primary and secondary amine groups.

The amphoteric polymers corresponding to the above definition may be chosen from the following polymers:

(1) polymers resulting from the copolymerization of at least one monomer derived from a vinyl compound bearing a carboxylic group, such as acrylic acid, methacrylic acid, maleic acid, α-chloroacrylic acid, and at least one basic monomer derived from a substituted vinyl compound comprising at least one basic atom, such as dialkylaminoalkyl methacrylate and acrylate, dialkylaminoalkylmethacrylamide and -acrylamide. Such compounds are described, for example, in U.S. Pat. No. 3,836,537.

Mention may also be made of the sodium acrylate/acrylamidopropyltrimethylammonium chloride copolymer sold under the name "Polyquart KE 3033" by the company Henkel.

The vinyl compound may also be a dialkyldiallylammonium salt such as dimethyldiallylammonium chloride. The copolymers of acrylic acid and of the latter monomer are sold under the names "Merquat 280," "Merquat 295" and "Merquat Plus 3330" by the company Calgon.

(2) polymers comprising units derived from:
a) at least one monomer chosen from acrylamides and methacrylamides substituted on the nitrogen with an alkyl radical,
b) at least one acidic comonomer comprising at least one reactive carboxylic group, and
c) at least one basic comonomer such as esters comprising substituents chosen from primary, secondary, tertiary and quaternary amine substituents of acrylic and methacrylic acids and the product of quaternization of dimethylaminoethyl methacrylate with dimethyl or diethyl sulphate.

In one embodiment, the N-substituted acrylamides or methacrylamides are, for example, groups in which the alkyl radicals comprise from 2 to 12 carbon atoms, such as N-ethylacrylamide, N-tert-butylacrylamide, N-tert-octylacrylamide, N-octylacrylamide, N-decylacrylamide, N-dodecylacrylamide and the corresponding methacrylamides.

The acidic comonomers are chosen, for example, from acrylic acids, methacrylic acids, crotonic acids, itaconic acids, maleic acids and fumaric acids and alkyl monoesters, comprising 1 to 4 carbon atoms, of maleic or fumaric acids or anhydrides.

The basic comonomers are chosen, for example, from aminoethyl, butylaminoethyl, N,N'-dimethylaminoethyl and N-tert-butylaminoethyl methacrylates.

The copolymers having the CTFA (4th edition, 1991) name octylacrylamide/acrylates/butylaminoethyl methacrylate copolymer such as the products sold under the name Amphomer or Lovocryl 47 by the company National Starch can be used.

(3) crosslinked and alkylated polyamino amides partially or totally derived from polyamino amides of general formula:

$$\mathrm{-\!\!\!+\!\!CO\!-\!R_{19}\!-\!CO\!-\!Z\!\!+\!\!\!-} \quad (X)$$

wherein $R_{19}$ is chosen from divalent radicals derived from saturated dicarboxylic acids, mono- and dicarboxylic aliphatic acids comprising at least one ethylenic double bond, esters of lower alkanols, comprising 1 to 6 carbon atoms, of these acids and radicals derived from the addition of any one of the acids of amines chosen from bis(primary) and bis (secondary) amines, and Z is chosen from bis(primary), mono- and bis(secondary) polyalkylene-polyamine radicals and, for example, Z represents:

a) in proportions ranging from 60 to 100 mol %, the radical of formula (XI):

$$\mathrm{-\!\!\underset{H}{N}\!\!+\!\!(CH_2)_X\!-\!\underset{H}{N}\!\!+\!\!\!-_P} \quad (XI)$$

wherein x=2 and p=2 or 3, or x=3 and p=2, this radical being derived from a compound chosen from diethylenetriamine, triethylenetetraamine and dipropylenetriamine;

b) in proportions ranging from 0 to 40 mol %, the radical (XI) above in which x=2 and p=1 and which is derived a compound chosen from ethylenediamine, and piperazine:

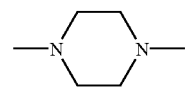

c) in proportions of from 0 to 20 mol %, the —NH—$(CH_2)_6$—NH— radical, which is derived from hexamethylenediamine, these polyamino amides being crosslinked by addition of a difunctional crosslinking agent chosen from epihalohydrins, diepoxides, dianhydrides and bis-unsaturated derivatives, using from 0.025 to 0.35 mol of crosslinking agent per amine group of the polyamino amide and alkylated by the action of acrylic acid, chloroacetic acid or an alkane sultone, and salts thereof.

In one embodiment, the saturated carboxylic acids are chosen from acids comprising 6 to 10 carbon atoms, such as adipic acid, 2,2,4-trimethyladipic acid and 2,4,4-trimethyladipic acid, terephthalic acid and acids comprising an ethylenic double bond such as, for example, acrylic acid, methacrylic acid and itaconic acid.

The alkane sultones used in the alkylation are chosen, for example, from propane sultone and butane sultone, and the salts of the alkylating agents can be chosen, for example, from the sodium or potassium salts.

(4) polymers comprising zwitterionic units of formula (XII):

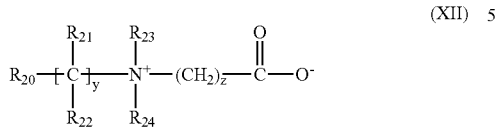
(XII)

wherein $R_{20}$ is derived from polymerizable unsaturated groups such as acrylate, methacrylate, acrylamide and methacrylamide groups, y and z, which may be identical or different, are chosen from integers ranging from 1 to 3, $R_{21}$ and $R_{22}$, which may be identical or different, are chosen from a hydrogen atom, methyl, ethyl and propyl groups, $R_{23}$ and $R_{24}$, which may be identical or different, are chosen from a hydrogen atom and alkyl radicals such that the sum of the carbon atoms in $R_{23}$ and $R_{24}$ does not exceed 10.

The polymers comprising such units can also comprise units derived from non-zwitterionic monomers such as monomers chosen from dimethyl and diethylaminoethyl acrylates, methacrylates, alkyl acrylates, acrylamides, methacrylamides, and vinyl acetate.

By way of example, mention may be made of the copolymer of butyl methacrylate/dimethylcarboxymethylammonioethylmethacrylate such as the product sold under the name "Diaformer Z301" by the company Sandoz.

(5) polymers derived from chitosan comprising monomer units corresponding to formulae (XIII), (XIV) and (XV) below:

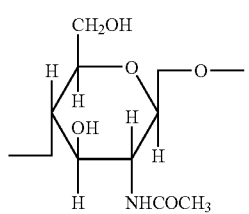
(XIII)

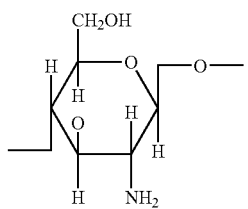
(XIV)

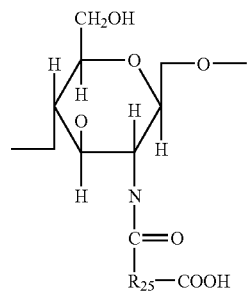
(XV)

the unit (XIII) being present in proportions ranging from 0 to 30%, the unit (XIV) in proportions ranging from 5% to 50% and the unit (XV) in proportions ranging from 30% to 90%, wherein in unit (XV), $R_{25}$ is a radical of formula:

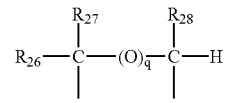

wherein q is chosen from 0 and 1.

If q=0, $R_{26}$, $R_{27}$ and $R_{28}$, which may be identical or different, are each chosen from a hydrogen atom, methyl, hydroxyl, acetoxy and amino residues, and monoalkylamine residues and dialkylamine residues which are optionally interrupted by at least one nitrogen atom and/or optionally substituted with at least one amine, hydroxyl, carboxyl, alkylthio and sulphonic groups, and alkylthio residues in which the alkyl group bears an amino residue, at least one of the radicals $R_{26}$, $R_{27}$ and $R_{28}$ being, in this case, a hydrogen atom; or, if q=1, $R_{26}$, $R_{27}$ and $R_{28}$, which may be identical or different, are each chosen from a hydrogen atom and salts formed by these compounds with bases or acids.

(6) polymers derived from the N-carboxyalkylation of chitosan, such as N-carboxymethylchitosan or N-carboxybutylchitosan sold under the name "Evalsan" by the company Jan Dekker.

(7) polymers corresponding to the general formula (XVI) as described, for example, in French Patent No. 1 400 366:

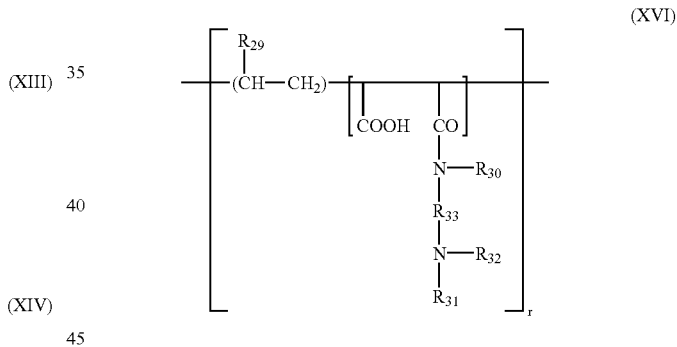
(XVI)

wherein $R_{29}$ is chosen from a hydrogen atom, and $CH_3O$, $CH_3CH_2O$ and phenyl radicals, $R_{30}$ is chosen from a hydrogen atom and lower alkyl radicals, such as methyl and ethyl, $R_{31}$ is chosen from a hydrogen and lower alkyl radicals, such as methyl and ethyl, $R_{32}$ is chosen from lower alkyl radicals, such as methyl and ethyl and radicals corresponding to the formula: $-R_{33}-N(R_{31})_2$, wherein $R_{33}$ is chosen from $-CH_2-CH_2-$, $-CH_2-CH_2-CH_2-$ and $-CH_2-CH$ $(CH_3)-$ groups, and $R_{31}$ is chosen from a hydrogen atom and lower alkyl radicals, such as methyl and ethyl, and also the higher homologues of these radicals comprising up to 6 carbon atoms, r is chosen such that the number-average molecular weight of said polymer ranges from 500 to 6 000 000, such as from 1000 to 1 000 000.

(8) amphoteric polymers of the type $-D-X-D-X-$ chosen from:
a) polymers obtained by the action of chloroacetic acid or sodium chloroacetate on compounds comprising at least one unit of formula:

$$-D-X-D-X-D- \quad (XVII)$$

wherein D is a radical

and X is chosen from the symbols E and E', wherein E and E', which may be identical or different, are chosen from divalent alkylene radicals comprising at least one chain chosen from straight and branched chains comprising up to 7 carbon atoms in the main chain, wherein the divalent alkylene radicals are optionally substituted with at least one hydroxyl group. E or E' can additionally comprise at least one atom chosen from oxygen, nitrogen and sulphur atoms, and 1 to 3 rings chosen from aromatic and heterocyclic rings. The oxygen, nitrogen and sulphur atoms can be present in the form of at least one group chosen from ether, thioether, sulphoxide, sulphone, sulphonium, alkylamine and alkenylamine, hydroxyl, benzylamine, amine oxide, quaternary ammonium, amide, imide, alcohol, ester and urethane groups;

b) polymers of formula:

—D—X—D—X— (XVIII)

wherein D is a radical

and X is chosen from the symbol E and E' and wherein at least one X is chosen from E'; E having the meaning given above and E' is chosen from divalent alkylene radicals comprising at least one chain chosen from straight and branched chains comprising up to 7 carbon atoms in the main chain, wherein said divalent alkylene radicals are optionally substituted with at least one hydroxyl radical and comprise at least one nitrogen atom substituted with an alkyl chain, which is optionally interrupted by an oxygen atom, wherein said alkyl chain comprises at least one functional group chosen from carboxyl functional groups and hydroxyl functional groups which are betainized by reaction with a reactant chosen from chloroacetic acid and sodium chloroacetate.

(9) ($C_1$–$C_5$)alkyl vinyl ether/maleic anhydride copolymers partially modified by semiamidation with an N,N-dialkylaminoalkylamine such as N,N-dimethylaminopropylamine or by semiesterification with an N,N-dialkanolamine. These copolymers can also comprise other vinyl comonomers such as vinylcaprolactam.

In one embodiment, the at least one amphoteric polymer is chosen from polymers comprising those of family (1).

The concentration of the at least one amphoteric polymer may range, for example, from 0.01% to 10% by weight, for example from 0.05% to 5% by weight and, as yet another example, from 0.1% to 3% by weight relative to the total weight of the composition.

In another embodiment, the compositions of the invention can further comprise at least one surfactant.

The at least one surfactant may be chosen from anionic, amphoteric, nonionic, zwitterionic and cationic surfactants.

The at least one surfactant employed can be chosen from, for example, the following:

(i) Anionic Surfactants

The at least one anionic surfactant may be chosen, for example, from salts, such as alkali metal salts, for example sodium salts, ammonium salts, amine salts, amino alcohol salts and magnesium salts of the following compounds: alkyl sulphates, alkyl ether sulphates, alkylamido ether sulphates, alkylarylpolyether sulphates, monoglyceride sulphates; alkyl sulphonates, alkyl phosphates, alkylamide sulphonates, alkylaryl sulphonates, α-olefin sulphonates, paraffin sulphonates; ($C_6$–$C_{24}$)alkyl sulphosuccinates, ($C_6$–$C_{24}$)alkyl ether sulphosuccinates, ($C_6$–$C_{24}$)alkylamide sulphosuccinates; ($C_6$–$C_{24}$)alkyl sulphoacetates; ($C_6$–$C_{24}$)acyl sarcosinates; and ($C_6$–$C_{24}$)acyl glutamates. The at least one anionic surfactant may be chosen, for example, from ($C_6$–$C_{24}$)alkylpolyglycoside carboxylic esters such as alkylglucoside citrates, alkylpolyglycoside tartrates and alkylpolyglycoside sulphosuccinates, alkylsulphosuccinamates; acyl isethionates and N-acyl taurates. The alkyl or acyl radical of these different compounds may comprise, for example, from 12 to 20 carbon atoms and the aryl radical may be chosen from, for example, phenyl and benzyl groups. Among the anionic surfactants which can be used mention may also be made, by way of nonlimiting examples, fatty acid salts such as oleic, ricinoleic, palmitic and stearic acid salts, coconut oil acid or hydrogenated coconut oil acid and their salts; acyl lactylates, wherein the acyl radical comprises from 8 to 20 carbon atoms. It is also possible to use alkyl D-galactoside uronic acids and their salts, polyoxyalkylenated ($C_6$–$C_{24}$)alkyl ether carboxylic acids, polyoxyalkylenated ($C_6$–$C_{24}$)alkylaryl ether carboxylic acids, polyoxyalkylenated ($C_6$–$C_{24}$)alkylamido ether carboxylic acids and their salts, for example, those comprising from 2 to 50 alkylene oxide groups, such as ethylene oxide groups, and mixtures thereof.

(ii) Nonionic Surfactant

The nonionic surfactants are compounds that are well-known (see, for example, in this respect "Handbook of Surfactants" by M. R. Porter, published by Blackie & Son (Glasgow and London), 1991, pp. 116–178). They can be chosen, for example, from polyethoxylated and polypropoxylated alkylphenols, alpha-diols and alcohols, comprising a fatty chain comprising, for example, 8 to 18 carbon atoms, it being possible for the number of ethylene oxide or propylene oxide groups to range, for example, from 2 to 50. Mention may also be made of copolymers of ethylene oxide and of propylene oxide, condensates of ethylene oxide and of propylene oxide with fatty alcohols; polyethoxylated fatty amides comprising, for example, from 2 to 30 mol of ethylene oxide, polyglycerolated fatty amides comprising on average from 1 to 5, such as 1.5 to 4, glycerol groups; polyethoxylated fatty amines comprising, for example, from 2 to 30 mol of ethylene oxide; oxyethylenated fatty acid esters of sorbitan comprising from 2 to 30 mol of ethylene oxide; fatty acid esters of sucrose, fatty acid esters of polyethylene glycol, alkylpolyglycosides, N-alkylglucamine derivatives, and amine oxides such as ($C_{10}$–$C_{14}$)alkylamine oxides or N-acylaminopropylmorpholine oxides.

(iii) Amphoteric or Zwitterionic Surfactant

The at least one amphoteric or zwitterionic surfactant may be chosen, for example, from aliphatic secondary and tertiary amine derivatives wherein the aliphatic radical is chosen from linear and branched chains comprising 8 to 18 carbon atoms and comprising at least one water-solubilizing anionic group (for example carboxylate, sulphonate, sulphate, phosphate or phosphonate); mention may also be made of $(C_8-C_{20})$alkylbetaines, sulphobetaines, $(C_8-C_{20})$ alkylamido$(C_1-C_6)$alkylbetaines or $(C_8-C_{20})$alkylamido $(C_1-C_6)$alkylsulphobetaines.

Among the amine derivatives, mention may be made of the products sold under the name Miranol, as described in U.S. Pat. Nos. 2,528,378 and 2,781,354 and classified in the CTFA dictionary, 3rd edition, 1982, under the names amphocarboxyglycinates and amphocarboxypropionates, with the respective structures:

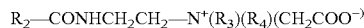

wherein: $R_2$ is chosen from alkyl radicals derived from acids $R_2$—COOH present in hydrolysed coconut oil, and heptyl, nonyl and undecyl radicals, $R_3$ is a beta-hydroxyethyl group and $R_4$ is a carboxymethyl group; and of

wherein:
B represents —$CH_2CH_2OX'$, C represents —$(CH_2)_z$—Y', with z=1 or 2,
X' is chosen from the —$CH_2CH_2$—COOH group and a hydrogen atom,
Y' is chosen from the —COOH and the —$CH_2$—CHOH—$SO_3H$ radicals,
$R_{2'}$ is chosen from alkyl radicals of an acid $R_2$—COOH present in coconut oil or in hydrolysed linseed oil, alkyl radicals, such as $C_7$, $C_9$, $C_{11}$ and $C_{13}$ alkyl radicals, a $C_{17}$ alkyl radical and its iso form, and an unsaturated $C_{17}$ radical.

These compounds are classified in the CTFA dictionary, 5th edition, 1993, under the names disodium cocoamphodiacetate, disodium lauroamphodiacetate, disodium caprylamphodiacetate, disodium capryloamphodiacetate, disodium cocoamphodipropionate, disodium lauroamphopropionate, disodium caprylamphodipropionate, disodium caprylamphodipropionate, lauroamphodipropionic acid and cocoamphodipropionic acid.

By way of example, mention may be made of the cocoamphodiacetate sold under the trade name Miranol® C2M concentrate by the company Rhodia Chimie.

(iv) Cationic Surfactant

The at least one cationic surfactant may be chosen, for example, from: salts of optionally polyoxyalkylenated primary, secondary and tertiary fatty amines; quaternary ammonium salts such as tetraalkylammonium, alkylamidoalkyltrialkylammonium, trialkylbenzylammonium, trialkylhydroxyalkylammonium and alkylpyridinium chlorides and bromides; imidazoline derivatives; and amine oxides of cationic nature.

The amount of the at least one surfactant present in the composition can range, for example, from 0.01% to 40% by weight such as from 0.5% to 30% by weight relative to the total weight of the composition.

The pH of the ready-to-use compositions may be, for example, from 1.5 to 12.

The pH of the ready-to-use compositions intended for bleaching may be, for example, from 1.5 to 10, such as from 1.5 to 7.

The pH of the ready-to-use compositions intended for permanent reshaping may be, for example, from 6 to 12, such as from 7 to 11.

This pH may be adjusted to the desired value using at least one acidifying agent and/or at least one basifying agent chosen from acidifying agents and basifying agents that are well-known in the art in the bleaching or permanent reshaping of keratin fibres.

The at least one basifying agent may be chosen from, for example, aqueous ammonia, alkali metals and ammonium carbonates, alkanolamines, such as monoethanolamine, diethanolamine and triethanolamine and their derivatives, oxyethylenated and oxypropylenated hydroxyalkylamines and ethylenediamines, sodium hydroxide, potassium hydroxide, and the compounds of formula (XIX) below:

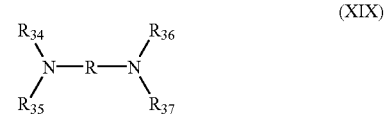

wherein R is a propylene residue optionally substituted with a group chosen from a hydroxyl group and $C_1-C_4$ alkyl radicals; $R_{34}$, $R_{35}$, $R_{36}$ and $R_{37}$, which may be identical or different, are chosen from a hydrogen atom, $C_1-C_4$ alkyl radicals, and $C_1-C_4$ hydroxyalkyl radicals.

The at least one acidifying agent is chosen from, for example, mineral acids and organic acids, such as hydrochloric acid and orthophosphoric acid, carboxylic acids, such as tartaric acid, citric acid and lactic acid, and sulphonic acids.

The at least one acidifying agent and the at least one basifying agent may each range from 0.01% to 30% by weight of the total weight of the bleaching or permanent-reshaping composition.

The compositions may also comprise sequestering agents, such as ethylenediaminetetraacetic acid (EDTA).

When the compositions comprising the at least one reducing agent and the at least one aminosilicone are in anhydrous form (e.g., in a powder or cream), they may comprise at least one agent chosen from the agents mentioned above in the form of essentially anhydrous solids and/or liquids and at least one additive chosen from the additives mentioned above in the form of essentially anhydrous solids or liquids.

When the medium comprising the at least one reducing agent is aqueous, it may comprise at least one cosmetically acceptable organic solvent chosen from, for example, alcohols, such as ethanol, isopropyl alcohol, benzyl alcohol and phenylethyl alcohol, polyols and polyol ethers, such as ethylene glycol monomethyl, monoethyl and monobutyl ethers, propylene glycol and its ethers, such as propylene glycol monomethyl ether, butylene glycol, dipropylene glycol, and diethylene glycol alkyl ethers, such as diethylene glycol monoethyl ether and monobutyl ether. The at least one solvent may be present in concentrations ranging from 0.5% to 20% by weight, such as from 2% to 10% by weight relative to the total weight of the composition.

The bleaching or permanent-reshaping compositions may also comprise an effective amount of at least one agent chosen from agents that are known in the art of bleaching or permanent reshaping of human keratin fibres, such as hair.

Needless to say, a person skilled in the art will take care to select the optional additional compound(s) mentioned above, such that at least one of the advantageous properties intrinsically associated with the composition for bleaching or permanently reshaping keratin fibres is not, or is not substantially, adversely affected by the envisaged addition(s).

The bleaching process comprises, for example, applying the ready-to-use reducing composition to wet or dry keratin fibres, leaving the composition to act for an action time, for example, ranging from 1 to 60 minutes, such as ranging from 10 to 45 minutes, optionally rinsing the fibres, optionally washing them with shampoo, optionally rinsing them again, and optionally drying them.

The permanent-reshaping process comprises, for example, applying the ready-to-use reducing composition to wet or dry keratin fibres, leaving the composition to act for an action time, for example, ranging from 1 to 60 minutes, such as ranging from 10 to 45 minutes, optionally rinsing the fibres, applying an oxidizing composition, leaving it to act for an action time ranging from 1 to 20 minutes, such as ranging from 1 to 10 minutes, optionally washing the fibres with shampoo, optionally rinsing them, and optionally drying them.

Mechanical means for placing the keratin fibres under tension may be used before, during and/or after applying the reducing composition, and may be removed before and/or after rinsing out the oxidizing composition.

Examples of new embodiments described herein are indicated below without, however, being limiting in nature.

EXAMPLE 1

The ready-to-use aqueous bleaching composition below was prepared (amounts expressed as grams of active material):

| | | |
|---|---|---|
| Citric acid | 7.4 | |
| Trisodium citrate dihydrate | 1 | |
| Hydroxyethylcellulose | 1.5 | |
| 2-Oxoglutaric acid | 0.8 | |
| Sodium ascorbate | 5.7 | |
| L-cysteine | 2 | |
| Polydimethylsiloxane of formula (I) Belsil ADM 652 ® from Wacker. | 2 | |
| Magnesium sulphate | 1 | |
| Water qs | 100 | |

The above bleaching composition allowed hair to be bleached, giving it a soft, smooth feel, a shiny appearance and good disentangling.

EXAMPLE 2

The reducing composition below was prepared: (expressed as grams of active material):

| | |
|---|---|
| Thioglycolic acid | 9.2 |
| Arginine | 15 |
| Aqueous ammonia comprising 20% NH3 | 1.86 |
| Ammonium carbonate | 4.5 |
| Cocoylamidopropylbetaine/glyceryl monolaurate (25/5) as an aqueous 30% solution Peptizer | 1.3 |
| Polydimethylsiloxane of formula (II): SLM 28020 ® from the company Wacker | 2 |
| Isostearyl alcohol (Tego Alkanol 66 sold by the company Goldschmidt) | 12 |
| Sequestering agent | 0.4 |
| Fragrance | 0.4 |
| Demineralized water qs | 100 |

This reducing composition was applied to a lock of wet hair, rolled up beforehand on a curler 9 mm in diameter.

After leaving the composition to act for ten minutes, the lock was rinsed thoroughly with water.

An oxidizing composition (8 volumes aqueous hydrogen peroxide solution of pH=3) was then applied.

After leaving the composition to act for ten minutes, the lock was again rinsed thoroughly with water. The hair was then unrolled from the roller and dried.

The hair showed good curl while being soft, smooth, shiny and easy to disentangle.

What is claimed is:

1. A cosmetic composition for treating keratin fibres comprising, in a cosmetically acceptable medium:
   (i) at least one reducing agent, and
   (ii) at least one aminosilicone chosen from formulae (I) and (II):

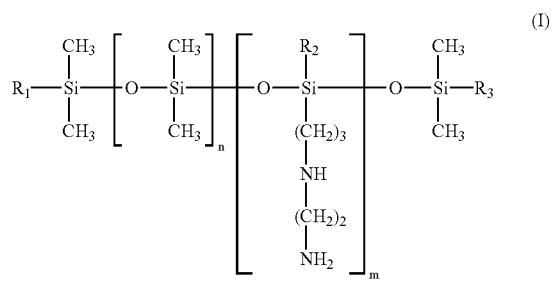

wherein:

m and n are numbers with a sum (n+m) ranging from 1 to 1000, n is a number ranging from 0 to 999, and m is a number ranging from 1 to 1000; and $R_1$, $R_2$ and $R_3$, which may be identical or different, are chosen from a hydroxyl radical and $C_1$–$C_4$ alkoxy radicals, at least one of the radicals $R_1$ to $R_3$ being an alkoxy radical; and

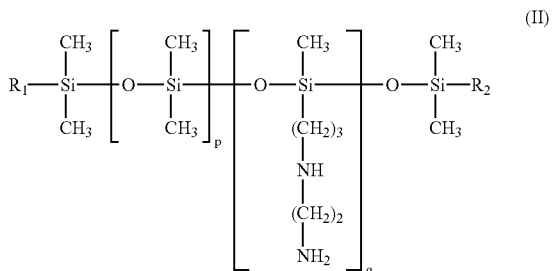

wherein:

p and q are numbers with a sum (p+q) ranging from 1 to 1000, p is a number ranging from 0 to 999 and q is a number ranging from 1 to 1000; and $R_1$ and $R_2$, which are different, are chosen from a hydroxyl radical and $C_1$–$C_4$ alkoxy radicals, at least one of the radicals $R_1$ and $R_2$ being an alkoxy radical.

2. The composition according to claim 1, wherein the keratin fibres are hair.

3. The composition according to claim 1, wherein the sum (m+n) ranges from 50 to 250.

4. The composition according to claim 1, wherein the sum (m+n) ranges from 100 to 200.

5. The composition according to claim 1, wherein n ranges from 49 to 249.

6. The composition according to claim 1, wherein n ranges from 125 to 175.

7. The composition according to claim 1, wherein m ranges from 1 to 10.

8. The composition according to claim 1, wherein m ranges from 1 to 5.

9. The composition according to claim 1, wherein the sum (p+q) ranges from 50 to 350.

10. The composition according to claim 1, wherein the sum (p+q) ranges from 150 to 250.

11. The composition according to claim 1, wherein p ranges from 49 to 349.

12. The composition according to claim 1, wherein p ranges from 159 to 239.

13. The composition according to claim 1, wherein q ranges from 1 to 10.

14. The composition according to claim 1, wherein q ranges from 1 to 5.

15. The composition according to claim 1, wherein the $C_1$–$C_4$ alkoxy radical is a methoxy radical.

16. The composition according to claim 1, wherein the at least one aminosilicone is chosen from formula (I) and has a hydroxyl/alkoxy molar ratio ranging from 0.2:1 to 0.4:1.

17. The composition according to claim 1, wherein the at least one aminosilicone is chosen from formula (I) and has a hydroxyl/alkoxy molar ratio ranging from 0.25:1 to 0.35:1.

18. The composition according to claim 1, wherein the at least one aminosilicone is chosen from formula (I) has a hydroxyl/alkoxy molar ratio of 0.3:1.

19. The composition according to claim 1, wherein the at least one aminosilicone is chosen from formula (II) and has a hydroxyl/alkoxy molar ratio ranging from 1:0.8 to 1:1.1.

20. The composition according to claim 1, wherein the at least one aminosilicone is chosen from formula (II) and has a hydroxyl/alkoxy molar ratio ranging from 1:0.9 to 1:1.

21. The composition according to claim 1, wherein the at least one aminosilicone is chosen from formula (II) and has a hydroxyl/alkoxy molar ratio of 1:0.95.

22. The composition according to claim 1, wherein the at least one aminosilicone is chosen from formula (I) and has a weight-average molecular mass ranging from 2000 to 1 000 000.

23. The composition according to claim 1, wherein the at least one aminosilicone is chosen from formula (I) and has a weight-average molecular mass ranging from 3500 to 200 000.

24. The composition according to claim 1, wherein the at least one aminosilicone is chosen from formula (II) and has a weight-average molecular mass ranging from 2000 to 200 000.

25. The composition according to claim 1, wherein the at least one aminosilicone is chosen from formula (II) and has a weight-average molecular mass ranging from 5000 to 100 000.

26. The composition according to claim 1, wherein the at least one aminosilicone is chosen from formula (II) and has a weight-average molecular mass ranging from 10 000 to 50 000.

27. The composition according to claim 1, wherein the at least one aminosilicone is in the form of an oil-in-water emulsion and further comprises at least one surfactant.

28. The composition according to claim 27, wherein the at least one surfactant is chosen from cationic and nonionic surfactants.

29. The composition according to claim 27, wherein the particle size of the at least one aminosilicone in the emulsion ranges from 3 to 500 nanometres.

30. The composition according to claim 29, wherein the particle size of the at least one aminosilicone in the emulsion ranges from 5 to 60 nanometres.

31. The composition according to claim 30, wherein the particle size of the at least one aminosilicone in the emulsion ranges from 10 to 50 nanometres.

32. The composition according to claim 1, wherein the at least one aminosilicone is chosen such that the contact angle with water of hair treated with a composition comprising 2% AM (active materials) of said at least one aminosilicone ranges from 90 to 180°.

33. The composition according to claim 32, wherein the at least one aminosilicone is chosen such that the contact angle with water of hair treated with a composition comprising 2% AM (active materials) of said aminosilicone ranges from 90 to 130°.

34. The composition according to claim 1, wherein the composition comprising at least one aminosilicone is chosen such that a contact angle of hair treated with said composition ranges from 90 to 180°.

35. The composition according to claim 1, wherein the at least one aminosilicone is present in an amount ranging from 0.01% to 20% by weight, relative to the total weight of the composition.

36. The composition according to claim 35, wherein the at least one aminosilicone is present in an amount ranging from 0.1% to 15% by weight, relative to the total weight of the composition.

37. The composition according to claim 36, wherein the at least one aminosilicone is present in an amount ranging from 0.5% to 10% by weight, relative to the total weight of the composition.

38. The composition according to claim 1, wherein the at least one reducing agent is chosen from thiols; thioglycolic acid and thiolactic acid, salts thereof and esters thereof; cysteamine and its salts; sulphites; ascorbic acid, its salts and its esters; and erythorbic acid, and its salts and its esters.

39. The composition according to claim 38, wherein the thiol is cysteine.

40. The composition according to claim 1, wherein the at least one reducing agent is present in an amount ranging from 0.1 to 30% by weight, relative to the total weight of the composition.

41. The composition according to claim 40, wherein the at least one reducing agent is present in an amount ranging from 0.5% to 20% by weight, relative to the total weight of the composition.

42. The composition according to claim 1, wherein said composition is anhydrous and is effective in bleaching or permanent reshaping the keratin fibre.

43. The composition according to claim 42, wherein the anhydrous composition is in pulverulent form.

44. A process for preparing a composition for treating keratin fibres comprising at least one aminosilicone chosen from formulae (I) and (II):

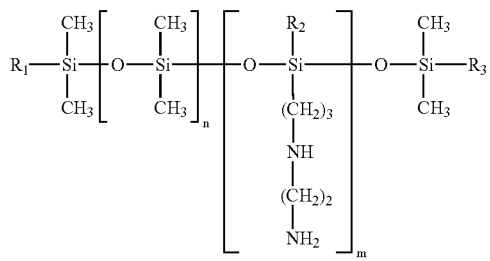

(I)

wherein:

m and n are numbers with a sum (n+m) ranging from 1 to 1000, n is a number ranging from 0 to 999, and is a number from 1 to 1000; and $R_1$, $R_2$ and $R_3$, which may be identical or different, are chosen from a hydroxyl radical and $C_1$–$C_4$ alkoxy radicals, at least one of the radicals $R_1$ to $R_3$ being an alkoxy radical; and

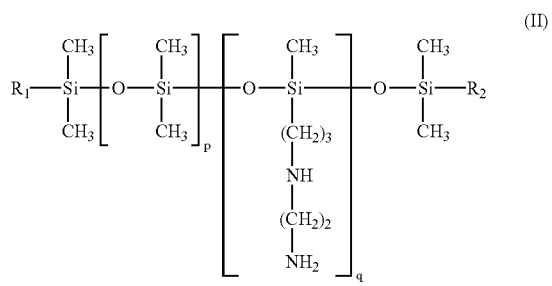

(II)

wherein:

p and q are numbers with a sum (p+q) ranging from 1 to 1000, p is a number ranging from 0 to 999 and q is a number ranging from 1 to 1000; and $R_1$ and $R_2$, which are different, are chosen from a hydroxyl radical and $C_1$–$C_4$ alkoxy radicals, at least one of the radicals $R_1$ and $R_2$ being an alkoxy radical, said process comprising combining extemporaneously, at the time of use, an anhydrous composition comprising at least one reducing agent with at least one aqueous composition, wherein at least one of the anhydrous or aqueous compositions comprises said at least one aminosilicone.

* * * * *